US007542854B2

(12) United States Patent
Kelkar et al.

(10) Patent No.: US 7,542,854 B2
(45) Date of Patent: Jun. 2, 2009

(54) METHOD FOR DISCOVERING GENE REGULATORY MODELS AND GENETIC NETWORKS USING RELATIONAL FUZZY MODELS

(75) Inventors: Bhooshan P. Kelkar, Flower Mound, TX (US); Rajiv D. Bendale, San Diego, CA (US)

(73) Assignee: International Business Machines Corporation, Armonk, NY (US)

( * ) Notice: Subject to any disclaimer, the term of this patent is extended or adjusted under 35 U.S.C. 154(b) by 321 days.

(21) Appl. No.: 10/897,339

(22) Filed: Jul. 22, 2004

(65) Prior Publication Data

US 2006/0020439 A1 Jan. 26, 2006

(51) Int. Cl.
*G06F 19/00* (2006.01)
*G06N 5/02* (2006.01)
(52) U.S. Cl. .......................................... 702/19; 706/46
(58) Field of Classification Search ....................... None
See application file for complete search history.

(56) References Cited

U.S. PATENT DOCUMENTS

| 5,414,797 | A | 5/1995 | Vassiliadis et al. |
| 5,819,242 | A | 10/1998 | Matsuoka et al. |
| 6,203,987 | B1 | 3/2001 | Friend et al. |
| 6,303,301 | B1 | 10/2001 | Mack |
| 6,338,051 | B1 | 1/2002 | Kang et al. |
| 6,340,565 | B1 | 1/2002 | Oliner et al. |
| 6,351,712 | B1 | 2/2002 | Stoughton et al. |
| 6,470,277 | B1 | 10/2002 | Chin et al. |
| 6,566,130 | B1 | 5/2003 | Srivastava et al. |
| 6,618,679 | B2 | 9/2003 | Loehrlein et al. |
| 6,633,659 | B1 | 10/2003 | Zhou |
| 6,980,974 | B2 * | 12/2005 | Kobayashi et al. ............ 706/21 |

| 2002/0029113 | A1 | 3/2002 | Wang et al. |

FOREIGN PATENT DOCUMENTS

| JP | 2002175305 A | 6/2002 |
| WO | WO 0238749 A1 | 5/2002 |
| WO | WO 0248352 A1 | 6/2002 |
| WO | WO 0248915 A1 | 6/2002 |
| WO | WO 03027262 A2 | 4/2003 |

OTHER PUBLICATIONS

Ressom, Physiol. Gemonics, 13:107-117 (2003).*
Ridley, Electronics Letters, 24(14) 890-892 (1998).*
Reynolds, Neural Network, 2001. Proceedings. IJCNN'01Int'l Conf., vol. 4, pp. 2738-2743 (2001).*
Merz, P. et al., "Clustering Gene Expression Profiles With Memetic Algorithms," Parallel Problem Solving from Nature, PPSN VII, 7th International Conference Proceedings, Lecture Notes in Computer Science vol. 2439, pp. 811-820, (2002).
"Automatic System for Inferring a Network from Gene Expression Profiles," Genome Infomatics 12, 2001, pp. 270-271, Horimoto.
Van Helden, Jacques et al., "Application of Regulatory Sequence Analysis and Metabolic Network Analysis to the Interpretation of Gene Expression Data," Computational Biology, First International Conference on Biology, Informatics, and Mathematics, JOBIM 2000, Computer Science, vol. 2066, 2001, pp. 147-163, Abstract, Dialog.
Chenaina, T. et al., "A Vectorial Space of Relationships Between Fuzzy Subsets for a Numerical Models of a Fuzzy Rules Bases," Joint Conference on Intelligent Systems, 1999 (JCIS 1998), vol. 1, pp. 191-194, Dialog Abstract.

* cited by examiner

*Primary Examiner*—Lori A Clow
(74) *Attorney, Agent, or Firm*—Norman Gundel; Hoffman Warnick LLC

(57) ABSTRACT

A method for discovering gene regulatory models using relational fuzzy models. A method is provided that includes clustering gene expression data into a set of clusters and identifying a representative subset of genes from the set of clusters; and building a relational fuzzy model using the representative subset.

3 Claims, 4 Drawing Sheets

Fuzzy interval M is defined as a tuple of five numbers:

$$M = \{m_1, m_2, \alpha, \beta, h\}$$

$$F(x) = \begin{cases} L(x), & x \leq m_1; \\ h, & m_1 \leq x \leq m_2; \\ R(x), & m_2 \leq x. \end{cases}$$

$$L(x) = \begin{cases} 0, & x < m_1 - \alpha; \\ [0, h], & m_1 - \alpha \leq x \leq m_1. \end{cases}$$

$$R(x) = \begin{cases} [0, h], & m_2 \leq x \leq m_2 + \beta; \\ 0, & x > m_2 + \beta. \end{cases}$$

METHOD FOR DISCOVERING GENE REGULATORY MODELS AND GENETIC NETWORKS USING RELATIONAL FUZZY MODELS

BACKGROUND OF THE INVENTION

1. Technical Field

The present invention relates generally to discovering gene regulatory models, and more specifically relates to a system and method for employing relational fuzzy modeling to evolve gene regulatory models based on gene expression data.

2. Related Art

Currently, tremendous efforts are being put forth in the fields of genomics, and more particularly, systems biology. Two important steps are involved in such an analysis. The first step involves gene expression analysis, which tries to determine what genes are active in the production of proteins. The second step involves gene regulatory models, which tries to determine the interdependence of active genes in the production of proteins. A significant challenge exists in developing algorithms to interpret the interdependence of different genes under different conditions.

Gene regulation can be useful for both assaying drugs and as a source for new molecular targets, assuming that regulatory models are well understood. Changes in gene expression patterns can be used to assay drug efficacy and for determining the onset of a disease. One assay that takes advantage of the existing level of sequence information and that is complementary to sequence and genetic analysis is gene expression profiling. Expression profiling technologies such as GENECHIP™ measure the expression level of thousands of genes simultaneously using an array of oligonucleotides bound to a silicon surface. These arrays are hybridized under stringent conditions with a complex sample representing mRNAs expressed in the test cell or tissue.

The results from these expression-profiling technologies are quantitative and highly parallel. These generate huge datasets that are not amenable to simple analysis. The greatest challenge in maximizing the use of this data is to use this data to develop algorithms to interpret and interconnect results for different genes under different conditions. Currently most expression data is analyzed using clustering, mining techniques or linear methods.

Examples include: 1. Cho et. al., "A Genome-wide transcriptional analysis of the mitotic cell cycle", Mol. Cell. 2: 65-73, 1998; 2. Tavazoie et. al, "Systematic determination of genetic network architecture," Nat Genet, 22:281-285, 1999; 3. Reconstructing Gene Networks from Large Scale Gene Expression Data. D'haeseleer, P., Ph.D. dissertation, University of New Mexico, 2000; 4. Genetic Network Inference: From Co-Expression Clustering to Reverse Engineering. D'haeseleer, P., Liang, S., and Somogyi, R., Bioinformatics 16(8):707-26, 2000; 5. Gene network inference using a linear, additive regulation model. D'haeseleer, P., Fuhrman, S., Submitted to Bioinformatics; 6. Linear Modeling of mRNA expression levels during CNS development and injury. D'haeseleer, P., Wen, X., Fuhrman, S., and Somogyi, R., *Pacific Symposium on Biocomputing* '99, pp. 41-52, World Scientific Publishing Co., 1999; 7. Gene Expression Analysis and Genetic Network Modeling. D'haeseleer, P., Liang, S., and Somogyi, R., Pacific Symposium on Biocomputing '99, Tutorial session on Gene Expression and Genetic Networks; 8. Data Requirements for Inferring Genetic Networks from Expression Data. D'haeseleer, P., Pacific Symposium on Biocomputing '99, Poster session; and 9. Mining the Gene Expression Matrix: Inferring gene relationships from large scale gene expression data. D'haeseleer, P., Wen, X., Fuhrman, S., and Somogyi, R., *Information Processing in Cells and Tissues*, Paton, R. C., and Holcombe, M. Eds., pp. 203-212, Plenum Publishing, 1998.

There have been other methods that make use of fuzzy logic that can enhance hard boolean logic based algorithms to do better clustering of gene expression data. Examples include: Tomida et al., "Gene Expression Analysis Using Fuzzy ART," Gen Infor, 12:245-246, 2001, which may be found on the world wide web at jsbi.org/journal/GIWO1/GIWO1POOS.pdf; Eisen et al., "Exploring the conditional co-regulation of yeast gene expression using fuzzy K-means clustering", Genome Biology, Vol_3:11, 1-6, 2002, which may be found on the world wide web at rana.lbl.gov/papers/Gasch GB 2002.pdf; and Delalin et al., "A fuzzy Algorithm for Gene Expression Analysis," which may be found on the world wide web at Iri.fr/~sebag/gafo/puces.pdf.

Unfortunately, significant drawbacks exist in linear, heuristic, regular or k-means clustering. Clustering, although powerful, can group data for only genes that express in a similar fashion. It identifies patterns only in genes that express in similar or different ways. The identification of genetic networks is however not so apparent from clustering. This drawback is dealt with in the paper, Woolf et.al., "A fuzzy logic approach to analyzing gene expression data," Physiol Genomics, 3:9-15, (2000), which uses fuzzy logic beyond just clustering to evolve gene regulatory models from gene expression data. However, in this case the models are built on heuristics and the rule based fuzzy logic is not really easily scalable.

Other techniques like neural networks can also address these issues and the use of neural networks for exploring gene expression data to evolve genetic networks has also been done, see, e.g., Keedwell E. et al., "Modeling gene regulatory data using artificial neural networks," Proc. of IJCNN'02, Honolulu, Hawaii, 183-188. However, the interpretation of the neural networks is not so easy for a scientist and hence this method is not suitable.

Accordingly, a need exists for an improved system and method of modeling gene regulatory data.

SUMMARY OF THE INVENTION

The present invention addresses the above-mentioned problems, as well as others, by providing a system, method and program product for discovering gene regulatory models using relational fuzzy logic. In a first aspect, the invention provides a system for discovering gene regulatory models, comprising: a data selection system that clusters gene expression data into a set of clusters and identifies a representative subset of genes from the set of clusters (and e.g., domain knowledge and other literature); and a relational fuzzy modeling system that builds a relational fuzzy model for the interdependence of genes using the representative subset.

In a second aspect, the invention provides a method for discovering gene regulatory models, comprising: clustering gene expression data to generate a set of clusters; identifying a representative subset of genes from the set of clusters (and e.g., domain knowledge and other literature); building a relational fuzzy model using the representative subset; and testing the relational fuzzy model on the gene expression data in the set of clusters.

In a third aspect, the invention provides a program product stored on a recordable medium for discovering gene regulatory models, comprising: means for clustering gene expression data to generate a set of clusters; means for identifying a representative subset of genes from the set of clusters and domain knowledge and other literature; means for building a relational fuzzy model using the representative subset; and means for testing the relational fuzzy model on the gene expression data in the set of clusters.

BRIEF DESCRIPTION OF THE DRAWINGS

These and other features of this invention will be more readily understood from the following detailed description of the various aspects of the invention taken in conjunction with the accompanying drawings in which.

DETAILED DESCRIPTION OF THE INVENTION

Figure 1:
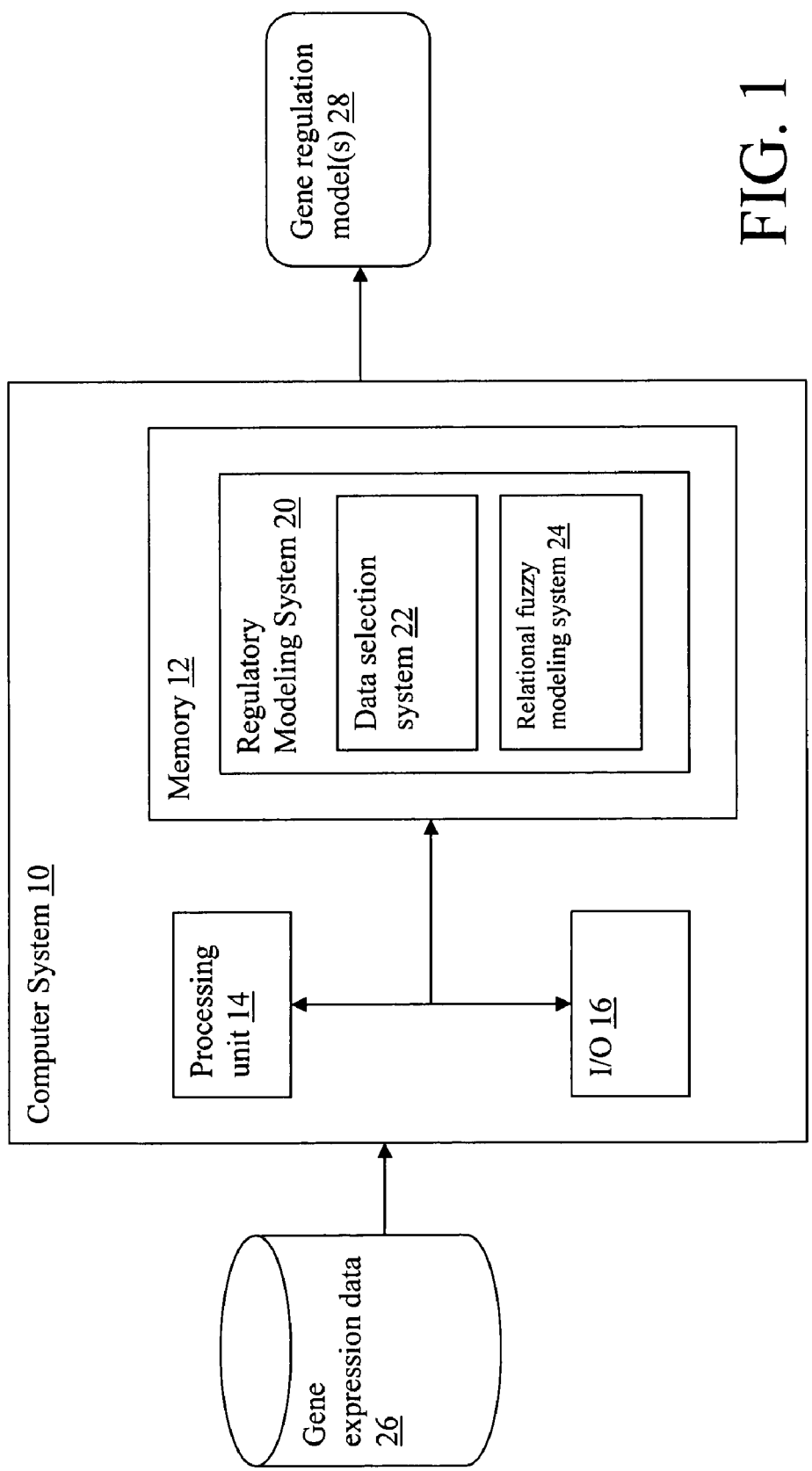
FIG. 1 depicts a computer system comprising a regulatory modeling system.

Referring now to the drawings, FIG. 1 shows a regulatory modeling system 20 embodied as a program product in a computer system 10. As described in further detail below, regulatory modeling system 20 processes a set of gene expression data 26 and generates one or more gene regulation models 28. To accomplish this, regulatory modeling system 20 includes a data selection system 22 and a relational fuzzy modeling system 24.

In general, computer system 10 may comprise, e.g., a desktop, a laptop, a workstation, etc. Moreover, computer system 10 could be implemented as part of a client and/or a server. Computer system 10 generally includes a processing unit 14, memory 12, a bus, input/output (I/O) interfaces 16, external devices/resources and storage. The processing unit 14 may comprise a single processing unit, or be distributed across one or more processing units in one or more locations, e.g., on a client and server. Memory 12 may comprise any known type of data storage and/or transmission media, including magnetic media, optical media, random access memory (RAM), read-only memory (ROM), a data cache, a data object, etc. Moreover, memory 12 may reside at a single physical location, comprising one or more types of data storage, or be distributed across a plurality of physical systems in various forms.

I/O interfaces 16 may comprise any system for exchanging information to/from an external resource. External devices/resources (not shown) may comprise any known type of external device, including speakers, a CRT, LED screen, hand-held device, keyboard, mouse, voice recognition system, speech output system, printer, monitor/display, facsimile, pager, etc. A bus may be included to provide a communication link between each of the components in the computer system 10 and likewise may comprise any known type of transmission link, including electrical, optical, wireless, etc. Although not shown, additional components, such as cache memory, communication systems, system software, etc., may be incorporated into computer system 10.

Gene expression database 26 may be embodied in any type of storage system (e.g., a relational database, etc.) and may include one or more storage devices, such as RAM, ROM, a magnetic disk drive and/or an optical disk drive. Database can also be distributed across, for example, a local area network (LAN), wide area network (WAN) or a storage area network (SAN) (not shown). Thus, database 26 could have some or all of their data stored remotely over a distributed network, thereby allowing for the pooling of resources and information.

Such a network could be any type of network such as the Internet, a local area network (LAN), a wide area network (WAN), a virtual private network (VPN), etc. Communication could occur via a direct hardwired connection (e.g., serial port), or via an addressable connection that may utilize any combination of wireline and/or wireless transmission methods. Moreover, conventional network connectivity, such as Token Ring, Ethernet, WiFi or other conventional communications standards could be used. Still yet, connectivity could be provided by conventional TCP/IP sockets-based protocol. In this instance, an Internet service provider could be used to establish interconnectivity. Further, as indicated above, communication could occur in a client-server or server-server environment.

It should be appreciated that the teachings of the present invention could be offered as a business method on a subscription or fee basis. For example, a computer system 10 comprising regulatory modeling system 20 could be created, maintained, supported and/or deployed by a service provider that offers the functions described herein for customers. That is, a service provider could offer the process of generating regulation models, e.g., as an application service provider.

Figure 2:
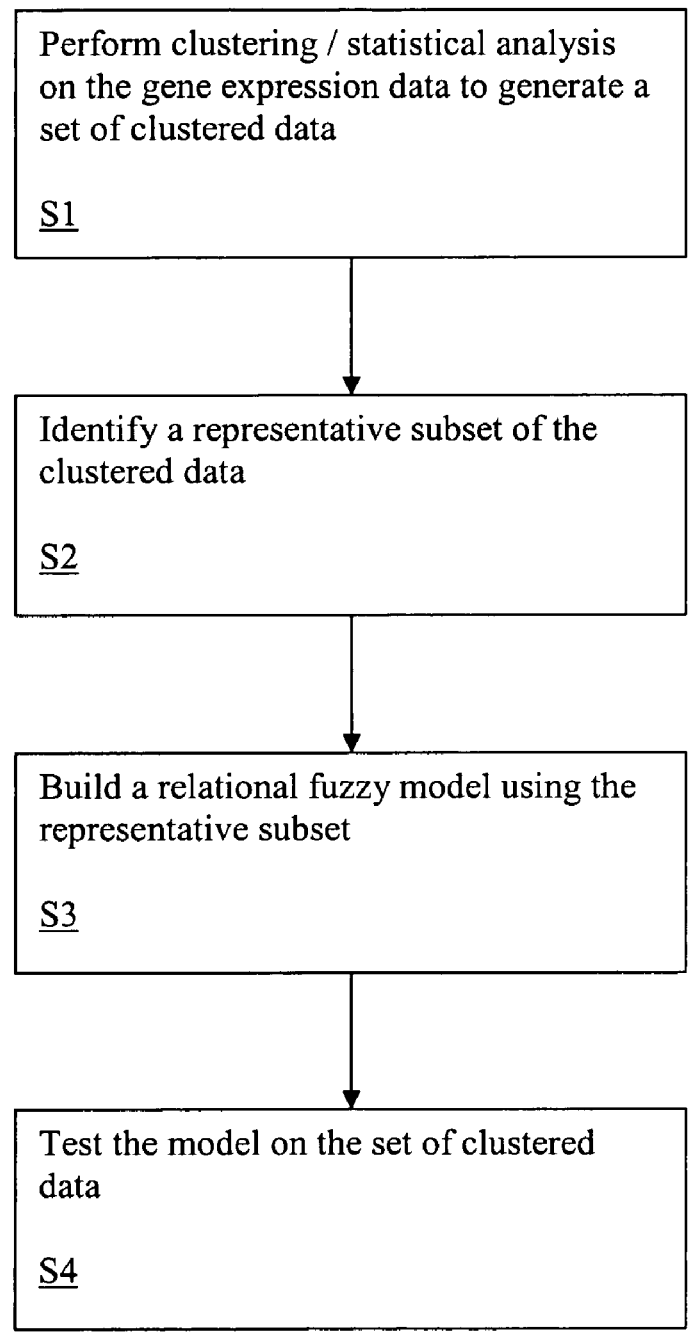
FIG. 2 depicts a flow diagram of the modeling system of FIG. 1.

Referring now to FIG. 2, a flow diagram depicting the overall operation of the regulatory modeling system is shown. In this first step S1, clustering (i.e., statistical analysis) of gene expression data is performed to generate a set of clustered gene expression data. Any known method for clustering can be utilized, such as SOMS, K-means, fuzzy k means, neural network based, etc. The result is a set of clusters in which each cluster has a defined cluster center and hence a representative point. Next, at step S2, a representative subset of the set of clusters is selected based on, e.g., domain knowledge, biology, previous results, heuristics, etc. For instance, if it is known that several of the genes in the set of clusters are related to food digestion, then those could be selected as the representative subset and/or additional genes could be added. Next, at step S3, a relational fuzzy model can be built using the representative subset to train the model. (Alternatively, a neural network based model could be built.) Finally, at step S4, the model can be tested on the original set of clustered data.

Thus, referring back to FIG. 1, data selection system 22 first performs a clustering operation to identify a set of clusters having cluster centers (i.e., representative points). Then, for a given model, e.g., an activator-repressor model, the clusters are labeled as clearly as possible, e.g., activator, repressor, etc. Next, a predefined percentage (or number) of representative points is considered for building a basic fuzzy model. The fuzzy model is built and compared with a known biological/domain knowledgebase and some more points are added if known. If such a knowledgebase is absent, then data is partitioned as per the necessity of the gene regulatory model.

Figure 3:
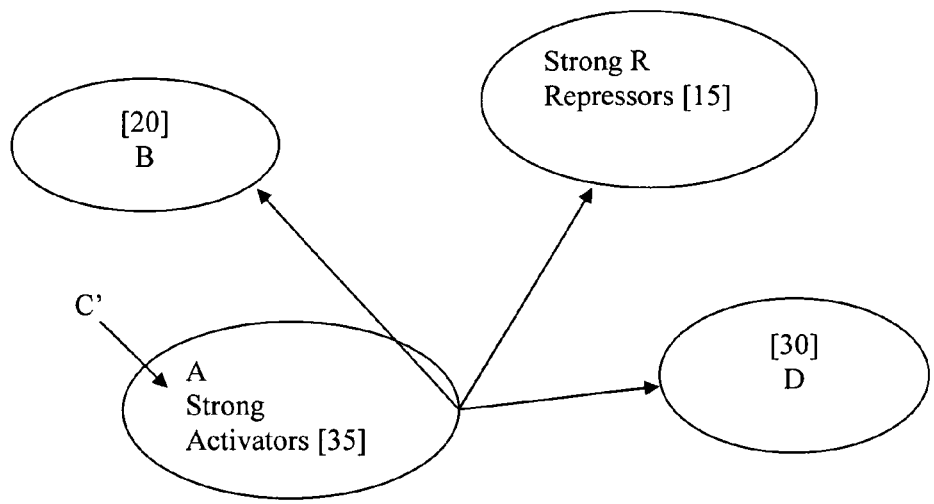
FIG. 3 depicts a clustering for separating genes in accordance with the present invention.

FIG. 3 shows an illustrative distribution of 100 genes in four clusters. In this example, assume that there exists a database of expression data having 100 genes, and some distance metric is used to come up with four clusters containing the 100 genes (e.g., 35 genes in (A), 20 genes in cluster (B), 30 genes in cluster (D), and 15 genes in (R)). Assume that the goal is to build a very simple model of a controlled gene (C') which belongs to (A), based on activator (A') and repressor model (R'). Then, it is generally known that C=f (A'/R'). To build the model for a gene using 35% of the data that has a "C'," one can select genes in the sets A, B and D for activators but not from R, since they have already been labeled as repressors. This saves a substantial amount of computation that would have otherwise been wasted.

For the same C=A/R model for 100 genes, theoretically one could use 100 choose 3 combinations, which is 100*99*98. Alternatively, one could build the model with almost the same accuracy using 50% of the data, since we can build at least an approximate model using the 50% of data in strong activator and strong repressor model. Assume the goal is to build a more complex gene regulatory model of C=A1*A2/R1*R2. This has two activators and two repressors. Clearly, the model must be rebuilt for other methods reported in literature and that is computationally intensive since the model is now complex. The method described herein is an efficient way to control the data volume handling without compromising on the quality since the grouping of the various genes is known.

Once the data is partitioned, relational fuzzy modeling system 24 is used to build the model and test it on the same data. A predefined set of top results can then be reported. This set of results would take the forms of activator/repressor gene combinations from the representative points from the identified clusters. For the purposes of this disclosure, it is assumed that the reader has a basic understanding of the principals of fuzzy modeling, and more specifically relational fuzzy modeling.

Use of relational fuzzy modeling is different from rule-based modeling in that it is data driven as opposed to rule based modeling in which one needs to setup the rules based on domain knowledge. Thus, rule based fuzzy modeling has a variety of shortcomings in terms of updating models, subjectivity inherent in the process, etc. Neural networks are better in that they are data driven and assume no knowledge of the system to be modeled. However, the output from a neural network is really a set of equations and is not easy for a scientist to interpret.

Figure 4:
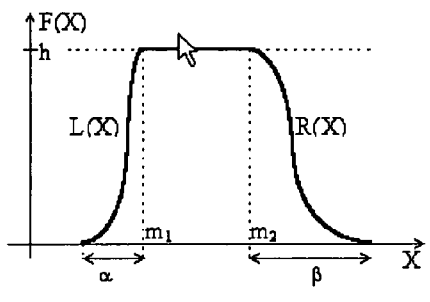
FIG. 4 depicts a fuzzy reference set.

In fuzzy logic, a fuzzy set A on universe X is defined by the ordered pair $(x, \mu_A(x))$, where x is the object on X, $\mu_A(x)$ is called the membership function of A. The membership function can be any value in the range of [0,1]. There are various types of fuzzy reference sets to describe the membership, one example is shown in FIG. 4.

The foundation of fuzzy modeling and control is the concept of the fuzzy set, first described by Zadeh in 1965. In dealing with their everyday lives, people tend to reason about the world in qualitative terms. For example, they will talk about 'tall' people, 'hot' water, 'fast' cars, etc. In all these adjectives, there is understood to be considerable ambiguity, and a common reference frame between people is required for them to successfully communicate. For example, a 'fast' car in the early years of motoring might have been one that could reach 30 mph, but this is certainly not what we would understand by the term today. Similarly if we want to have machines that are able to process qualitative information in the form of rules, then we have to have some means of stating the terms of reference.

The natural way of defining a reference frame is to group things into sets; thus one would have a set of tall people, a set of hot water temperatures, a set of fast cars, and so on. However, conventional sets have a sharp cutoff between an element belonging to the set and it not belonging. This does not fit in well with what people actually mean by these qualitative terms. For example, if we specify a conventional set of tall people we might fix a set boundary at 1.8 m. Now, with a conventional, or crisp, set someone who was 1.8 m would be classed as tall, but someone whose height was 1.799 m would not. This clearly is not the sort of meaning that a human would attach to the adjective 'tall'.

The fuzzy set is a way of dealing with real world ambiguity. A fuzzy set is a set with a fuzzy boundary, and the elements of the set belong to it with a variable grade of membership. This grade of membership is a number between zero and one, and it indicates how strongly a particular element belongs to the set (one indicating the strongest belonging and zero the weakest). For sets on continuous ranges (e.g., a range of real numbers) the membership of the set is defined by a membership function. For example, a fuzzy set of tall people might be defined so that everyone over 2.0 m in height belonged to the set with a grade of membership of one, everyone less than 1.5 m with a grade of membership of zero, and people between 1.5 m and 2.0 m in height with some, varying, intermediate grade of membership.

Fuzzy membership functions can be of any shape that the designer decides is appropriate for the particular situation. Usually, however, one of a small group of functions is used to describe a fuzzy set, and the most commonly used nowadays is the triangular membership function. A triangular membership function only requires the position of three points to be specified: the leftmost edge of the set; the vertex of the set where the grade of membership is equal to one; and the rightmost edge of the set. The set can be 'opened' on one side simply by specifying a set boundary extending to infinity (or, anyway, a very large number!)

For modeling purposes, we need to define a group of sets that describe the range of each variable of interest. For example, to describe the heights of a group of people we might decide to use three fuzzy sets with the linguistic tags small, medium and large. The group of fuzzy sets which are specified for each variable are called the reference sets for that variable.

The usual first step of processing in a fuzzy model or controller is the stage known as fuzzification. Here scalar values of the inputs are converted into possibility vectors. A possibility vector is simply a vector that describes the degree of membership of a particular input value in each of the reference sets defined for that input.

After fuzzification, the next stage is to process the fuzzy information in the possibility vectors through the rules describing the controller, or model, to form a fuzzy output possibility vector. To do this some compositional rules of inference are used to combine possibilities on both sides of any logical conditions. For example, a rule might say:

IF the person is tall AND the person is fit THEN the person can jump high.

In this case the possibilities for the person being tall and for the person being fit have to be combined across a logical AND to give the overall degree of truth for the rule. There are a variety of different sets of compositional rules, but one of the most popular sets is:

Across an AND: multiply the possibilities together; and
Across an OR: add the possibilities together (but fix the maximum value at 1).

Once the individual rules have been processed, we are left with a group of consequents from the rules giving values for the possibilities for the output lying in each of the output reference sets. Often several rules will have the same consequent (e.g., the person can jump high), but will have fired at different strengths. In these cases it is necessary to combine the rules by taking the maximum possibility for that consequent.

Figure 5:
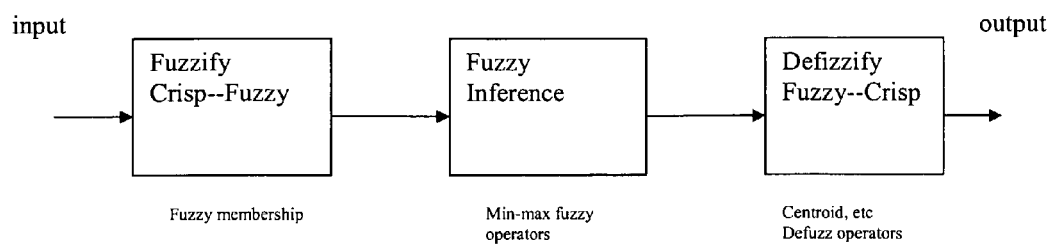
FIG. 5 depicts a fuzzy logic process.

The final step is then to convert the possibility vector for the output into a scalar value that can be used as, say, a signal to a control valve. Again, there have been several different methods suggested for carrying out defuzzification, but the most popular is the fuzzy mean. An overview of the fuzzy logic process is shown in FIG. 5.

Relational fuzzy modeling of gene expression data has advantages over traditional fuzzy modeling and can be implemented as follows. In analyzing genetic expression data, the data is transformed from crisp values to fuzzy values by fuzzification. A simplified set of gene expression data may appear as follows: Lets assume that gene expression values are ranging between 0-100.

|  | t1 | t2 | t3 | t4 |
|---|---|---|---|---|
| Gene 1 | 10 | 44 | 0 | 97 |
| Gene 2 | 18 | 19 | 6 | 88 |

Figure 6:
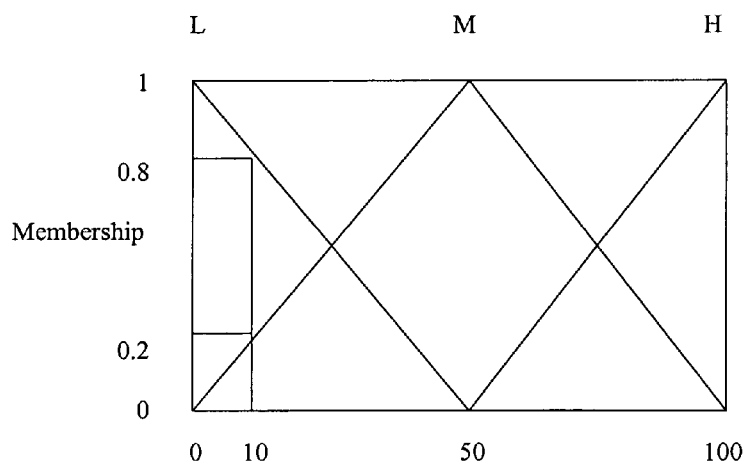
FIG. 6 depicts a degree of member ship for scalar values.

Fuzzification will replace each of the scalar values with a possibility vector that describes a degree of membership of each particular value. This is depicted in FIG. 6, where a scalar value of 10 would be converted using three triangular reference sets L, M and H as a fuzzy vector {0.8, 0.2, 0.0}. This triplet means that a value of 10 is represented as being Low with a Grade of truth of "0.8", "0.2" as Medium and "0.0" as high.

Then, triplets of data are used to fill in the relational fuzzy matrix that is initially filled with zeros. Any fuzzy operational algorithm could be used for the fuzzified values to fill the relational fuzzy matrix. This is done for all time stamps for the triplets. Then, the next triplet is used for updating this model as the base model.

Fuzzy relational systems differ from other fuzzy techniques in that a relational model has no explicit set of rules. Instead a relational array is used that maps every possible AND combination of the input reference sets to every output set. For example, consider a system with two inputs and a single output:

Output=f (Var1, Var2)

If two reference sets, e.g., Low and High, are defined for each input variable, then there are four combinations of input reference sets, and each of these have to be mapped onto each of the similar two output reference sets. Thus the relational array will consist of eight elements such as:

|  | Output set 1 | Output set 2 |
|---|---|---|
| Var1 (set a) | 0.2 | 0.5 |
| Var1 (set b) | 0.8 | 0 |
| Var2 (set a) | 0.2 | 0.1 |
| Var4 (set b) | 0.7 | 0.5 |

The content of each element in the relational array is a number between zero and one, which indicates how strong the particular relationship linked to that element is. A value of zero indicates that the relationship does not apply, but values greater than zero indicate an increasing strength in the relationship as they approach one. Since every possible relationship between the inputs and outputs is included in the relational array, the values of the relational array elements are what determine how the relational model behaves.

There are several ways of obtaining values for the relational array elements. One is simply to encode a rule-base into a relational format; in the simplest case this means that the array will hold values only of zero and one, since a rule either exists or it does not. Complications can arise with this approach, however, since rule antecedents are usually formulated with more flexibility than the relational model structure allows for.

Identification of the relational array directly from process input-output data is also possible, and this is the primary advantage that relational modeling has over its rule-based counterpart. There have been several identification algorithms proposed, but one of the best for noisy systems is that of Ridley, J. N., Shaw, I. S., and Kruger, J. J., "Probabilistic fuzzy model for dynamic systems," Electronic Letters, 24, (1988), pp 890-892, hereinafter "RSK." The RSK algorithm for this identification technique is:

$R(s1, \ldots, sn, s) = \{\text{SUM from } \{k=1\} \text{ to } Nf\_\{s1, \ldots, sn, k\}. Y(s)k\} \text{ over } \{\text{SUM from } \{k=1\} \text{ to } Nf\_\{s1, \ldots, sn, k\}\}$ where,

| | |
|---|---|
| $R(s1, \ldots, sn, s) =$ | An entry in the relational array |
| $sn =$ | The reference set index for the nth input |
| $s =$ | The reference set index for the output |
| $N =$ | Total number of samples of input-output data |
| $fs1, \ldots, sn, =$ | The product of the input possibilities in reference sets |
| $Yk =$ | Possibility vector for the output (at sample k) |

The key to the strength of this algorithm in dealing with noisy I/O data is the "f-factor," which gives a measure of the frequency of occurrence of each combination of inputs. The contribution of any particular sample of I/O data is thus weighted according to how frequently, and how strongly, that particular input combination is seen in the data. So, single examples of bad data are unlikely to have a significant effect on the values stored in the relational array.

It is understood that the systems, functions, mechanisms, methods, engines and modules described herein can be implemented in hardware, software, or a combination of hardware and software. They may be implemented by any type of computer system or other apparatus adapted for carrying out the methods described herein. A typical combination of hardware and software could be a general-purpose computer system with a computer program that, when loaded and executed, controls the computer system such that it carries out the methods described herein. Alternatively, a specific use computer, containing specialized hardware for carrying out one or more of the functional tasks of the invention could be utilized. In a further embodiment, part of all of the invention could be implemented in a distributed manner, e.g., over a network such as the Internet.

The present invention can also be embedded in a computer program product, which comprises all the features enabling the implementation of the methods and functions described herein, and which—when loaded in a computer system—is able to carry out these methods and functions. Terms such as computer program, software program, program, program product, software, etc., in the present context mean any expression, in any language, code or notation, of a set of instructions intended to cause a system having an information processing capability to perform a particular function either directly or after either or both of the following: (a) conversion to another language, code or notation; and/or (b) reproduction in a different material form.

The foregoing description of the invention has been presented for purposes of illustration and description. It is not intended to be exhaustive or to limit the invention to the precise form disclosed, and obviously, many modifications and variations are possible. Such modifications and variations that may be apparent to a person skilled in the art are intended to be included within the scope of this invention as defined by the accompanying claims.

The invention claimed is:

1. A computer-implemented method for generating gene regulatory models, comprising:

clustering gene expression data to generate a set of clusters;

identifying a subset of the gene expression data from within the set of clusters;

building a relational fuzzy model using the subset, wherein the building of the relational fuzzy model comprises using input and output data identified from the subset to build the relational fuzzy model without using rules based on domain knowledge, wherein the relational fuzzy model comprises a relational array that maps all possible relationships between the input and output data and for each possible relationship provides an indication of the strength in the relationship between the input and output data;

testing the relational fuzzy model on the gene expression data in the set of clusters;

using the relational fuzzy model to generate gene regulatory models; and outputting at least one display of the gene regulatory models;

wherein each of said method steps is performed on a computer.

2. The method of claim 1, further comprising using an identification algorithm to fill the relational array.

3. The method of claim 2, wherein the identification algorithm is defined as:

$$R(s1,\ldots,sn,s) = \{\text{SUM from}\{k=1\} \text{ to } Nf\_\{s1,\ldots,sn,k\}. Y(s) k\} \text{ over } \{\text{SUM from } \{k=1\} \text{ to } Nf\_\{s1,\ldots,sn,k\}\}$$

where,

| | |
|---|---|
| $R(s1,\ldots,sn,s) =$ | An entry in the relational array |
| $sn =$ | The reference set index for the nth input |
| $s =$ | The reference set index for the output |
| $N =$ | Total number of samples of input-output data |
| $fs1,\ldots,sn, =$ | The product of the input possibilities in reference sets |
| $Yk =$ | Possibility vector for the output (at sample k). |

* * * * *